United States Patent
Inada

(10) Patent No.: US 8,801,605 B2
(45) Date of Patent: Aug. 12, 2014

(54) ENDOSCOPE APPARATUS

(75) Inventor: Ayumu Inada, Tokyo (JP)

(73) Assignee: Olympus Corporation, Tokyo (JP)

( * ) Notice: Subject to any disclaimer, the term of this patent is extended or adjusted under 35 U.S.C. 154(b) by 68 days.

(21) Appl. No.: 13/476,244

(22) Filed: May 21, 2012

(65) Prior Publication Data

US 2012/0302832 A1    Nov. 29, 2012

(30) Foreign Application Priority Data

May 25, 2011 (JP) ................................ P2011-117171

(51) Int. Cl.
*A61B 1/00* (2006.01)
*A61B 1/005* (2006.01)

(52) U.S. Cl.
CPC ............... *A61B 1/005* (2013.01); *A61B 1/0052* (2013.01)
USPC ......................................... 600/146; 600/139

(58) Field of Classification Search
USPC ................. 600/103, 131, 109, 114, 146, 148; 348/75, 76; 359/803; 396/17; 165/11.2
See application file for complete search history.

(56) References Cited

U.S. PATENT DOCUMENTS

| | | | | |
|---|---|---|---|---|
| 5,322,518 A | * | 6/1994 | Schneider et al. | 604/247 |
| 7,780,593 B2 | * | 8/2010 | Ueno et al. | 600/146 |
| 2007/0276430 A1 | * | 11/2007 | Lee et al. | 606/205 |

FOREIGN PATENT DOCUMENTS

JP      2004-321492 A    11/2004

OTHER PUBLICATIONS

JP 2004-321492, Machine Translation including Bibliographic information, accessed from espacenet.com on Oct. 15, 2013, 17 pages total.*

* cited by examiner

*Primary Examiner* — Alireza Nia
*Assistant Examiner* — Timothy J Neal
(74) *Attorney, Agent, or Firm* — Holtz Holtz Goodman & Chick PC

(57) ABSTRACT

This endoscope apparatus includes: an insertion portion; a bending portion; an operation portion; and a pull member. The operation portion includes: an operation lever; a bearing that supports the operation lever in a state of being freely inclinable around a swinging center; a friction member that is fixed to the operation lever; a press portion configured to contact a contact surface; and a switching device that is connected to the press portion and presses the press portion against the contact surface when rotated in a first rotational direction with a predetermined rotation axis as a rotation center thereof and also so as to cause the press portion to be spaced away from the contact surface when rotated in a second direction.

11 Claims, 10 Drawing Sheets

ENDOSCOPE APPARATUS

BACKGROUND OF THE INVENTION

1. Field of the Invention

The present invention relates to an endoscope apparatus. Priority is claimed on Japanese Patent Application No. 2011-117171, filed on May 25, 2011, the content of which is incorporated herein by reference.

2. Description of the Related Art

Conventionally known endoscope apparatuses include ones for observing places that an observer is unable to see directly with his or her eyes such as the inside of an observation target.

For example. Japanese Unexamined Patent Application, First Publication No. 2004-321492 describes an endoscope apparatus including: a long insertion portion; a bending portion provided at a distal end of the insertion portion; and an operation portion provided at a proximal end of the insertion portion. The operation portion of the endoscope apparatus described in Japanese Unexamined Patent Application. First Publication No. 2004-321492 includes: a bending lever for bending the bending portion through an inclination operation; a frictional force retention portion for retaining an operation position of the bending portion with a frictional force; and a retention state release portion for releasing the bending lever retained at the operation position.

SUMMARY OF THE INVENTION

According to a first aspect of the present invention, an endoscope apparatus includes: a long insertion portion; a bending portion provided at a distal end of the insertion portion; an operation portion that performs a bending operation of the bending portion; and a pull member that connects the bending portion to the operation portion and is pulled through the bending operation by the operation portion, to thereby bend the bending portion. Furthermore, the operation portion includes: a joystick which is inclined about a predetermined swinging center and to which the bending operation is input; a bearing that supports the joystick in a state of being freely inclinable about the swinging center; a friction member that is fixed to the joystick and on which a contact surface is formed the contact surface being the swinging center; a press portion configured to contact the contact surface; and a switching device that is connected to the press portion and presses the press portion against the contact surface when rotated in a first rotational direction with a predetermined rotation axis as a rotation center thereof and also so as to cause the press portion to be spaced away from the contact surface when rotated in a second rotational direction.

According to a second aspect of the present invention, the press portion includes: a stick-like relay member that extends in a direction of the rotation axis; and a protrusion portion that protrudes from an external surface of the relay member outwardly in a radial direction of the relay member. Furthermore, the switching device includes a cam member in which a guide wall to engage the protrusion portion is formed as apart of a spiral about a central axis line of the relay member, and which rotates with respect to the relay member with the central axis line of the relay member as the rotation center.

According to a third aspect of the present invention, an external surface of the relay member has a cutout that extends in parallel with a central axis line of the relay member. A part of the pull member is contained in an internal portion of the cutout and is arranged in parallel with the central axis line of the relay member.

According to a fourth aspect of the present invention, the relay member has a through-hole that extends in parallel with the central axis line of the relay member and opens at both ends. Furthermore, a part of the pull member is inserted into the through-hole and is arranged in parallel with the central axis line of the relay member.

According to a fifth aspect of the present invention, the endoscope apparatus further includes a biasing member that biases the press portion toward the contact surface. Furthermore, when rotated in the second rotational direction, the switching device causes the press portion to be pulled away from the contact surface while resisting a biasing force of the biasing member.

DETAILED DESCRIPTION OF THE INVENTION (First Embodiment)

An endoscope apparatus 1 according to a first embodiment of the present invention will be described.

Figure 1:
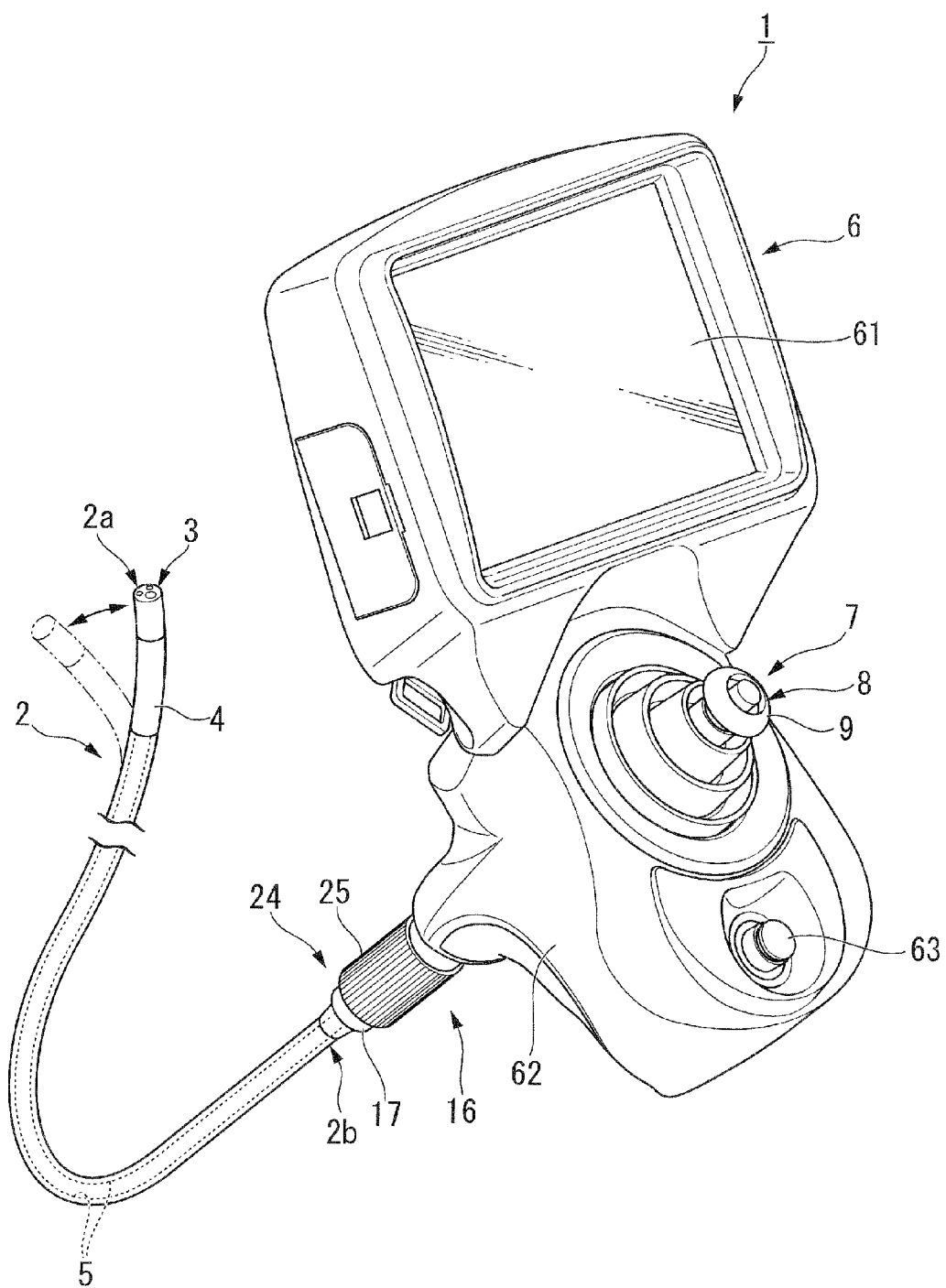
FIG. 1 is an overall view showing an endoscope apparatus of a first embodiment according to the present invention.
Figure 2:
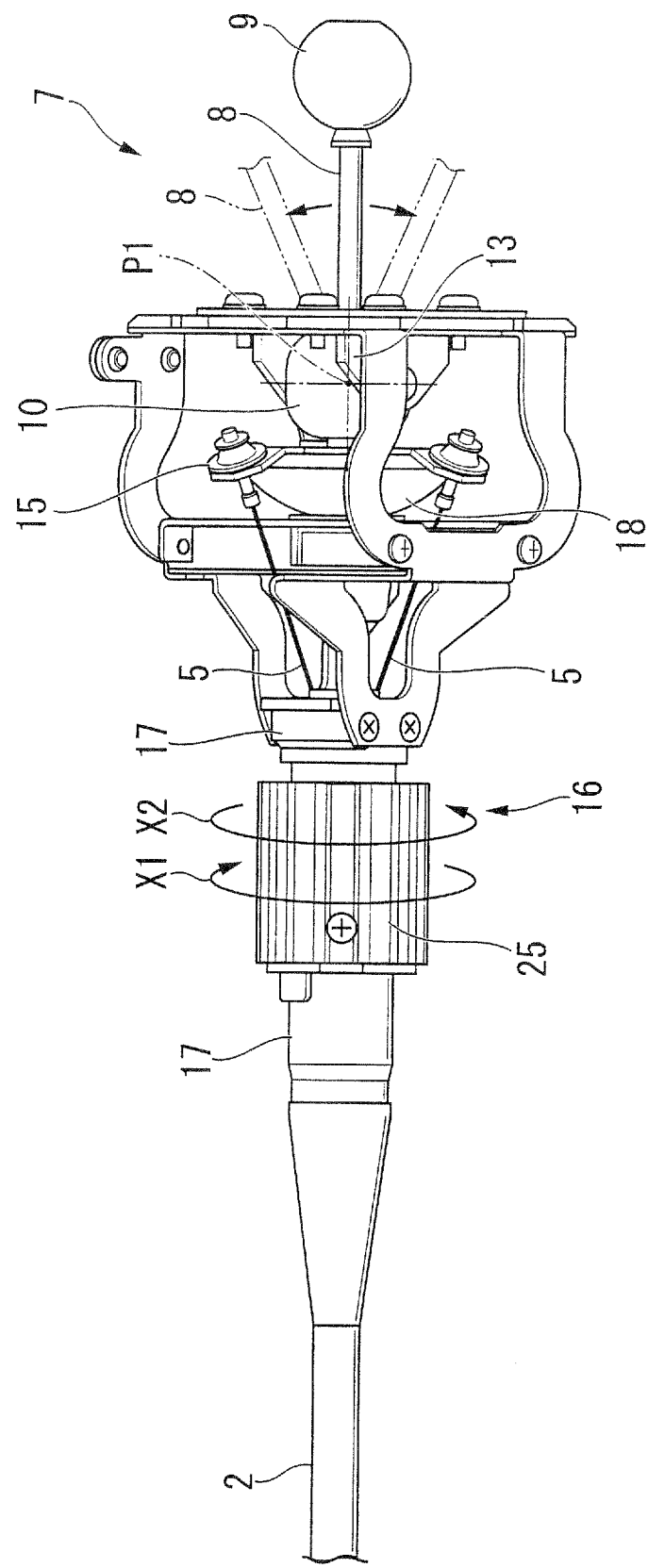
FIG. 2 is a side view showing a part of an internal configuration of an operation portion of the endoscope apparatus of the first embodiment.

Firstly, a configuration of the endoscope apparatus 1 according to the first embodiment of the present invention will be described. FIG. 1 is an overall view of the endoscope apparatus 1 of the first embodiment according to the present invention. FIG. 2 is a side view showing a part of an internal configuration of an operation portion 6 of the endoscope apparatus 1.

As shown in FIG. 1, the endoscope apparatus 1 includes: a long insertion portion 2; a bending portion 4 provided at a distal end 2a of the insertion portion 2; an operation portion 6 for performing a bending operation of the bending portion 4; and pull members 5 for coupling the bending portion 4 and the operation portion 6 to each other.

In the distal end 2a of the insertion portion 2, there is provided an imaging mechanism 3 for obtaining images of an observation target.

As the imaging mechanism 3, a known imaging mechanism that includes: an image sensor such as a CCD or a CMOS; and an optical system for forming an image of an observation target on the image sensor may be appropriately adopted. Furthermore, instead of including the imaging mechanism 3, it may be configured such that an image of the observation target is transmitted to the operation portion 6 through a bundle of optical fibers.

The bending portion 4 is a member for directing the imaging mechanism 3 in the distal end 2a of the insertion portion 2 to an intended direction. In addition, the bending portion 4 has a known configuration provided with a plurality of bender pieces, joint rings, or the like. In the first embodiment of the present invention, distal ends of the pull members 5 are fixed to the bending portion 4. The pull members 5 extend to the operation portion 6 through the bending portion 4 and the insertion portion 2.

As shown in FIG. 1 and FIG. 2, the operation portion 6 includes: an input portion 7 to which a bending operation for bending the bending portion 4 is input by the operator of the endoscope apparatus 1; and a bent state retention device 16 that retains the bending portion 4 in an intended bent state.

The input portion 7 includes: a stick-like bending lever 8 (a joystick) that is inclined about a predetermined swinging center P1; a bearing 13 that supports the bending lever 8 in a state of being freely inclinable about the swinging center P1; and a pull arm 15 that transmit the bending operation by the bending lever to the pull members 5.

As shown in FIG. 1, the bending lever 8 is arranged in a manner protruding from an external surface of the operation portion 6. At a protrusion end of the bending lever 8, there is provided a knob 9 that is to be pressed by a finger of the operator of the endoscope apparatus 1.

An end of the bending lever 8 opposite to the protrusion end is coupled to the bearing 13 via a swinging body 10.

Figure 3:
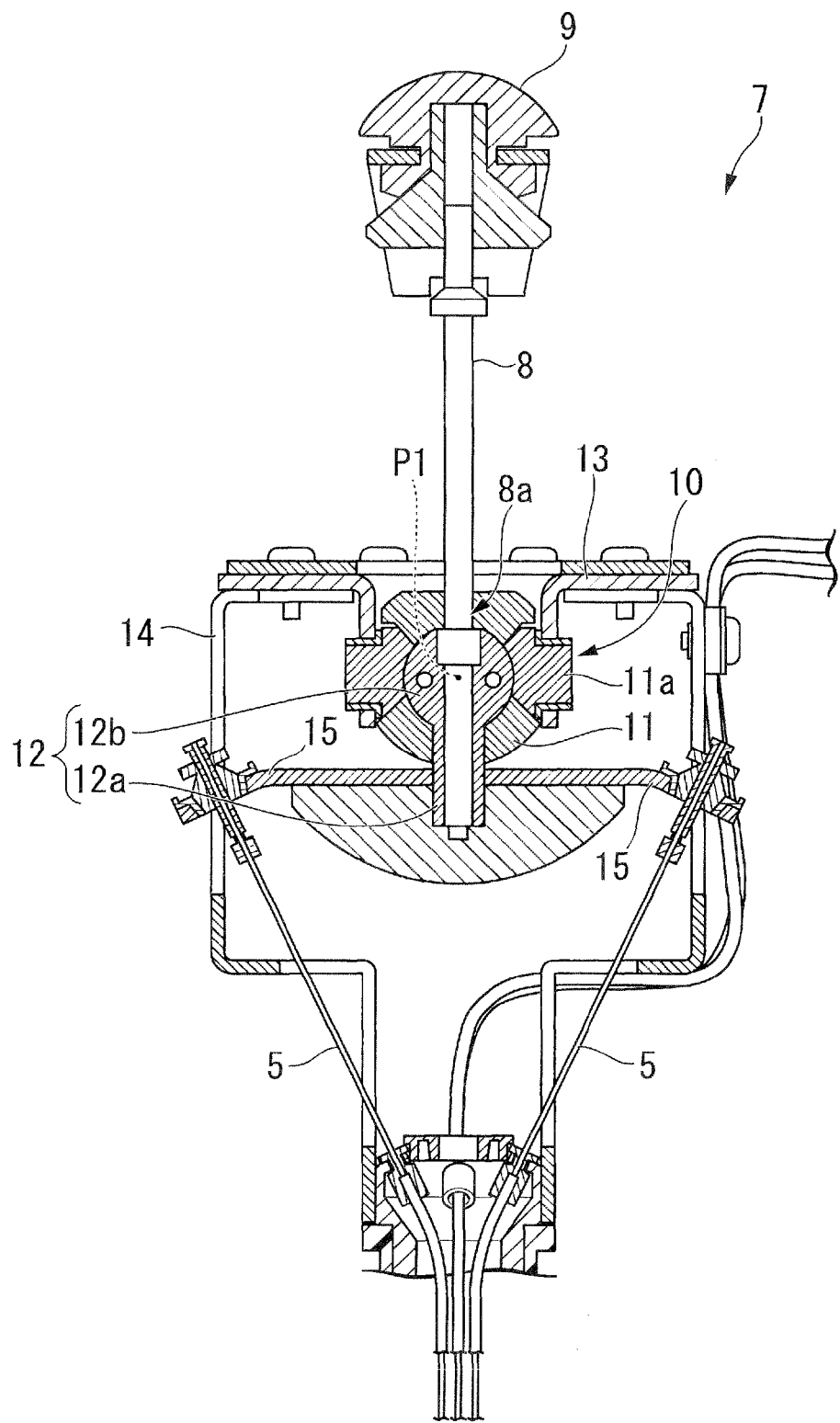
FIG. 3 is a partial cross-sectional view of the operation portion of the first embodiment.
Figure 4:
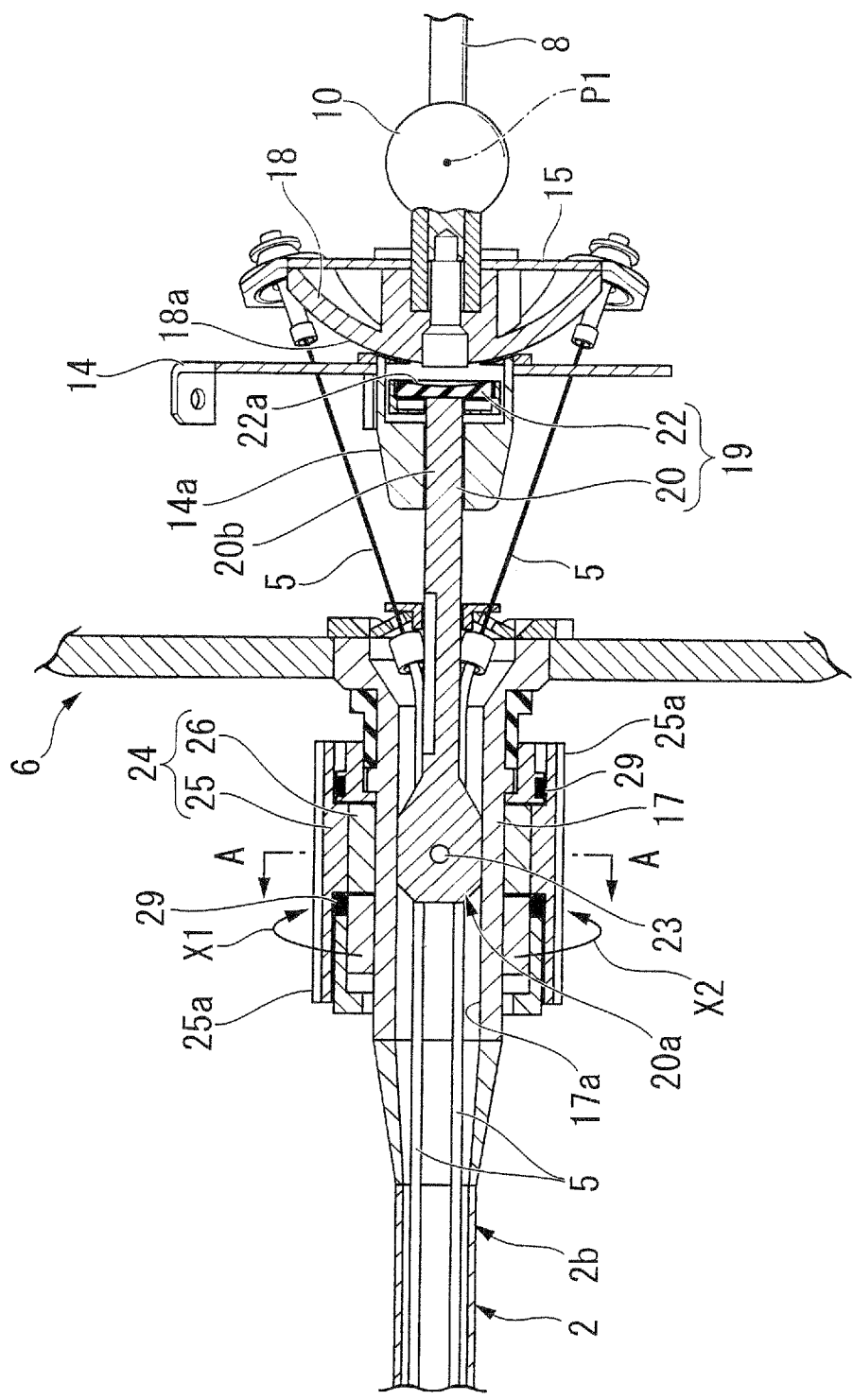
FIG. 4 is a partial cross-sectional view of the operation portion of the first embodiment.

FIG. 3 and FIG. 4 are partial cross-sectional views of the operation portion 6. In FIG. 3, illustration of some components of the bent state retention device 16 is omitted.

As shown in FIG. 3, the swinging body 10 includes: a first member 11 that is attached rotatably to the bearing 13; and a second member 12 that is attached rotatably to the first member 11.

The first member 11 is formed of metal, resin, or the like. The first member 11 has a rotary shaft portion 11a. The first member 11 rotates in a predetermined range about an axis line of the rotary shaft portion 11a. In the first member 11, there are formed cutouts so as to avoid interference with a shaft portion 12a and the bending lever 8, the shaft portion 12a provided in the second member 12, which will be described later.

The second member 12 is formed of metal, resin, or the like. It has: substantially-cylindrical shaft portion 12a; and a rotary shaft portion 12b that is formed in a substantially-cylindrical shape at one end of the shaft portion 12a. A central axis line of the shaft portion 12a and a central axis line of the rotary shaft portion 12b are orthogonal to each other. The second member 12 is attached to the first member 11 so that both of the axis line of the shaft portion 12a and the axis line of the rotary shaft portion 12b are orthogonal to a central axis line of the rotary shaft portion 11a of the first member 11.

A distal end 8a of the bending lever 8 is fixed to the rotary shaft portion 12b of the second member 12. When the bending lever 8 is inclined, the second member 12 can rotate in a predetermined range about the axis line of the rotary shaft portion 12b with respect to the first member 11.

The central axis line of the rotary shaft portion 11a and the central axis line of the rotary shaft portion 12h are orthogonal to each other. The point of intersection of the central axis line of the rotary shaft portion 11a and the central axis line of the rotary shaft portion 12b is the aforementioned swinging center P1.

The bearing 13 is formed on a frame 14 that supports the input portion 7 and the bent state retention device 16 in the operation portion 6. The bearing 13 is fixed to a casing of the operation portion 6 via the frame 14.

The pull arm 15 is fixed to the shaft portion 12a of the swinging body 10. The pull arm 15 extends in four directions orthogonal to the central axis line of the shaft portion 12a. Proximal ends of the pull arm 15 are fixed to each end portion of the pull arm 15 extending in each of the four directions.

As shown in FIG. 4, the bent state retention device 16 includes: a coupling member 17 that is interposed between the insertion portion 2 and the operation portion 6; a friction member 18 that is fixed to a shaft portion of the swinging body 10; a press portion 19 a part of which is inserted into the coupling member 17; and a switching device 24 that is attached to the coupling member 17.

Figure 5:
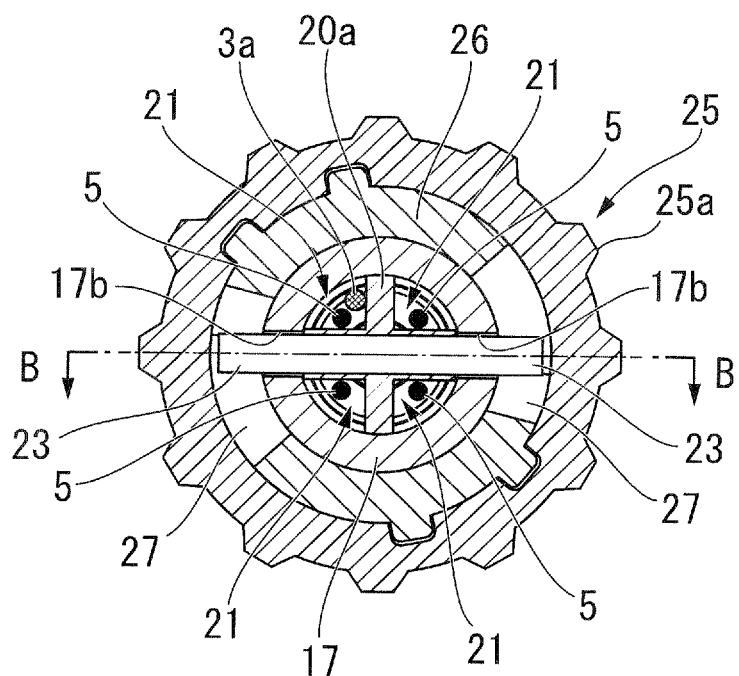
FIG. 5 is a cross-sectional view of FIG. 4, taken along the line A-A.
Figure 6:
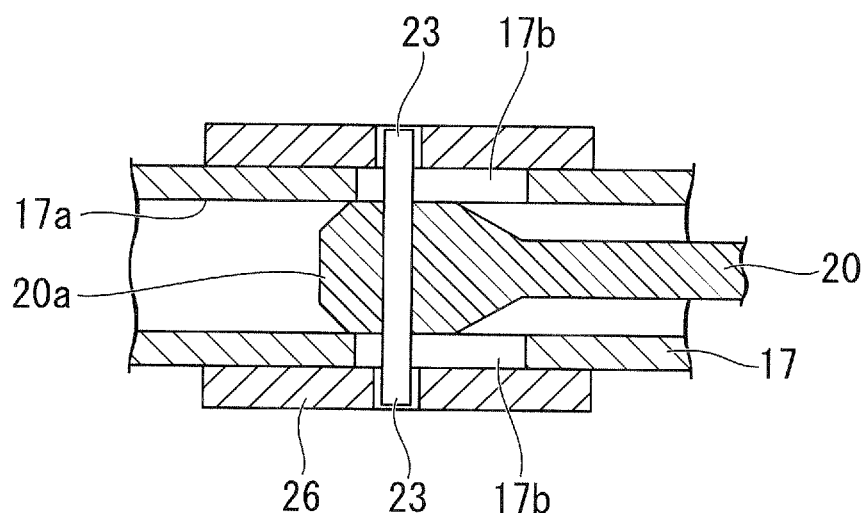
FIG. 6 is a cross-sectional view of FIG. 5, taken along the line B-B.

FIG. 5 is a cross-sectional view of FIG. 4, taken along the line A-A. FIG. 6 is a cross-sectional view of FIG. 5, taken along the line B-B.

As shown in FIG. 4 and FIG. 5, the coupling member 17 is a substantially-cylindrical member which is formed with a hole 17a for communicating an internal portion of the insertion portion 2 with an internal portion of the operation portion 6. A signal line 3a of the imaging mechanism 3, the press portion 19, and the pull members 5 are inserted inside the hole 17a.

As shown in FIG. 5 and FIG. 6, in the coupling member 17, there are formed elongated holes 17h that extend in a direction of the central axis line of the hole 17a and communicated between the inside and outside of the coupling member 17. Through the elongated holes 17b formed in the coupling member 17, there is inserted a protrusion portion 23, which will be described later.

Figure 7:
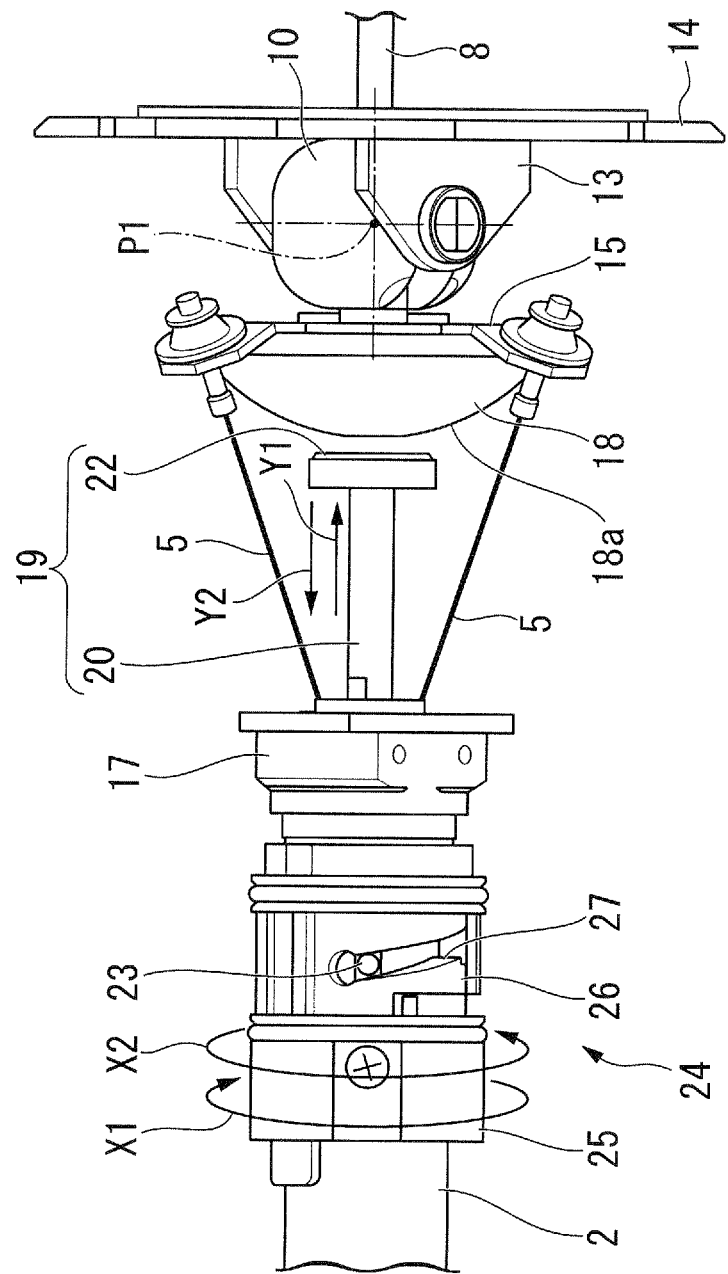
FIG. 7 is a side view showing a part of the internal configuration of the operation portion of the first embodiment.
Figure 8:
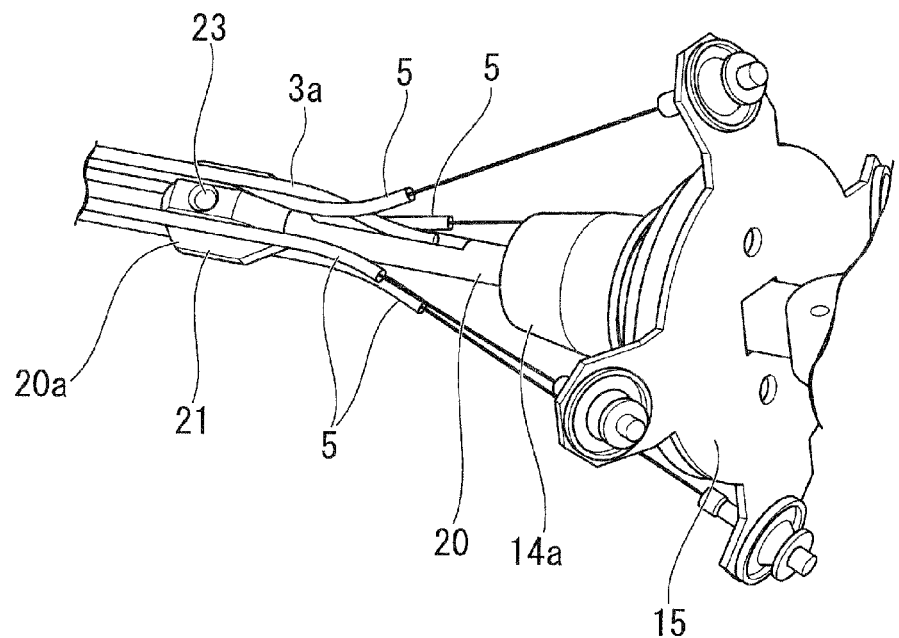
FIG. 8 is an oblique perspective view showing a part of the internal configuration of the operation portion of the first embodiment.

FIG. 7 and FIG. 8 are side views showing a part of the internal configuration of the operation portion 6.

As shown in FIG. 7, the coupling member 17 and the bending lever 8 are arranged so that the swinging center P1 of the bending lever 8 is positioned on an extension line of the central axis line of the hole 17a that is formed in the coupling member 17.

The friction member 18 is a member that is fixed to the shaft portion of the swinging body 10 and is formed with a contact surface 18a. The contact surface 18a forms a part of a spherical surface whose center is the swinging center P1. The contact surface 18a is subjected to a treatment for increasing the frictional force against the press portion 19, and/or is made of a combination of materials such that the coefficient of friction between itself and the press portion 19 is high.

As shown in FIG. 4, the press portion 19 includes: a stick-like relay member 20 that extends in a direction of the central axis line of the hole 17a (that is, a rotation axis of a switching grip 25, which will be described later) formed in the coupling member 17; a stopper member 22 that is fixed to a proximal end of the relay member 20 and has a curved surface 22a with a curvature so as to fit the curved shape of the contact surface 18a; and a protrusion portion 23 that protrudes externally in the radial direction of the relay member 20 from an external surface of the distal end of the relay member 20.

As shown in FIG. 5, an outer diameter of the relay member 20 at the distal end 20a is set so as to have clearance that allows the relay member 20 to freely advance or retract in the hole 17a of the coupling member 17.

As shown in FIG. 5 and FIG. 8, in the distal end 20a of the relay member 20, there are formed four cutouts 21 that extend in parallel with the central axis line of the relay member 20.

The four cutouts 21 are provided about the central axis line of the relay member 20 in a manner spaced 90 degrees apart.

In the four cutouts 21, the pull members 5 are contained respectively. As a result, in their parts contained in the cutouts 21 of the relay member 20, the pull members 5 are arranged in parallel with the central axis line of the relay member 20. In addition, the pull members 5 will not cross one another in the hole of the coupling member 17 because each pull member 5 is contained in each of the four cutouts 21.

Furthermore, in the first embodiment of the present invention, there is formed a hollow structure in the relay member 20 from its middle portion in the central axis direction to its proximal end portion, and the relay member 20 has an opening in a part of its middle portion. Through the hollow portion of the relay member 20, the signal line 3a of the imaging mechanism 3, other lead lines, and the like are inserted.

As shown in FIG. 4, a proximal end 20b of the relay member 20 is supported by the frame 14.

To be more precise, the frame 14 is provided with a housing 14a. In the housing 14a, there is formed a through-hole through which the relay member 20 is inserted so as to be capable of advancing or retracting. In the housing 14a, there is arranged a stopper member 22.

The stopper member 22 is a member that is pressed against the contact surface 18a into engagement with the contact surface 18a. The stopper member 22 is formed, for example, in a disk-like shape and is made from a resin material such as rubber. In the first embodiment of the present invention, the stopper member 22 has elasticity.

The stopper member 22 together with the relay member 20 is supported by the frame 14. As a result, when the press portion 19 is moved toward the proximal end in the direction of the central axis line of the hole 17a of the coupling member 17, the stopper member 22 is guided toward the swinging center P1 and contacts the contact surface 18a.

Because the curved surface 22a of the stopper member 22 is formed with a curvature to fit the curved shape of the contact surface 18a, the curved surface 22a and the contact surface 18a are brought into surface contact with each other.

The protrusion portion 23 is made of a pin that extends in the direction orthogonal to the central axis line of the relay member 20. In the first embodiment of the present invention, the protrusion portion 23 is formed longer than the outer diameter of the distal end of the relay member 20, and protrudes outside the coupling member 17 from the elongated holes 17b formed in the coupling member 17.

The switching device 24 includes: a cylindrical switching grip 5 that surrounds the outer circumference of the coupling member 17; and a cylindrical cam member 26 that is fixed to the switching grip 25.

The switching grip 25 is a member for the user of the endoscope apparatus 1 to grip by its outer circumferential surface and to rotate about the central axis line of the hole of the coupling member 17. On the outer circumference surface of the switching grip 25, there are formed linear ridges 25a that extend in parallel with the central axis line of the switching grip 25. These function as slip stoppers when the switching grip 25 is rotated.

Figure 9:
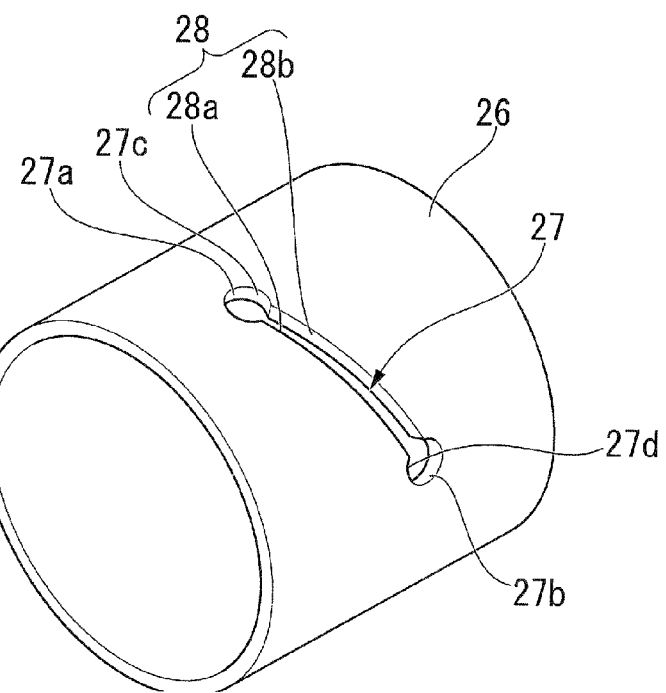
FIG. 9 is an oblique perspective view showing a cam member.

FIG. 9 is an oblique perspective view showing the cam member 26.

The cam member 26 is a member that is rotated integrally with the switching grip 25. As shown in FIG. 7 and FIG. 9, in the cam member 26, there is formed a guide wall 27 that is a part of a spiral extending about the central axis line of the relay member 20. In the first embodiment of the present invention, the guide wall 27 formed in the cam member 26 is an inner surface of a through-hole that penetrates an outer wall of the cam member 26 in the thickness direction of the cam member 26. Note that the guide wall 27 may be an inner surface of a groove with a bottom that is recessed from the inner surface of the cam member 26 toward the external surface of the cam member 26.

In the guide wall 27, an end 27a of the guide wall 27 on the distal end side of the cam member 26 and an end 27b of the guide wall 27 on the proximal end side of the cam member 26 are spaced less than or equal to 180° apart from each other in a peripheral direction of the cam member 26. In addition, the guide wall 27 has a length less than one turn in the circumferential direction of the cam member 26. As a result, when a transition is made from the state where the protrusion portion 23 is located at the end 27a at the distal end of the guide wall 27 to the state where the protrusion portion 23 is located at the end 27b at the proximal end of the guide wall 27, there is no need to re-grip the switching grip 25.

As shown in FIG. 7, the guide wall 27 has a pair of guide surfaces 28 facing, each other with a space therebetween into which a protruded end of the protrusion portion 23 provided in the relay member 20 can be inserted. Each of the pair of guide surfaces 28 engages the protrusion portion 23, and causes the protrusion portion 23 to advance or retract along the elongated holes of the coupling member 17. In the first embodiment of the present invention, when the protrusion portion 23 is moved to the proximal end side of the cam member 26, a surface 28a on the distal end side of the cam member 26 out of the pair of guide surfaces 28 guides the protrusion portion 23. When the protrusion portion 23 is moved to the distal end side of the cam member 26, a surface 28b on the proximal end side of the cam member 26 out of the pair of guide surface 28 guides the protrusion portion 23.

Furthermore, as shown in FIG. 7 and FIG. 9, at both ends 27a, 27b of the guide wall 27 in the spiral direction, there are respectively formed recess portions 27c, 27d into which the protrusion portion 23 is to be inserted. Of both ends of the guide wall 27, the recess portion 27d formed at the end on the proximal end side of the earn member 26 is formed in a shape recessed toward the distal end of the cam member 26.

As shown in FIG. 7, with the protrusion portion 23 being inserted into the guide wall 27 of the earn member 26, the switching device 24 is coupled to the press portion 19. When the switching grip 25 is rotated in a first rotational direction (a direction denoted with reference symbol X1 in FIG. 7) about the central axis line of the hole of the coupling member 17, the switching device 24 presses the stopper member 22 to the friction member 18 side (in a direction denoted with reference symbol Y1 in FIG. 7) via the relay member 20. Contrary to this, when the switching grip 25 is rotated in a second rotational direction (a direction denoted with reference symbol X2 in FIG. 7) of the rotation direction about the central axis line of the hole 17a of the coupling member 17, the switching device 24 pulls the stopper member 22 in a direction in which the stopper member 22 is spaced away from the friction member 18 (a direction denoted with reference symbol Y2 in FIG. 7), In the first embodiment of the present invention, the stopper member 22 is brought into contact with the contact surface 18a slightly before the protrusion portion 23 reached the recess portion 27d at the end 27b at the proximal end of the guide wall 27 formed in the cam member 26.

As shown in FIG. 4, two O rings 29 are provided between the inner circumferential surface of the switching grip 25 and the outer circumferential surface of the coupling member 17. One of the O rings 29 is arranged, on the distal end side of the cam member 26 and the other of the O rings 29 is arranged on the proximal end side of the cam member 26. The O rings 29 prevent liquid from going into the internal portion of the hole through the guide wall 27 formed in the cam member 26 and through the elongated holes formed in the coupling member 17. As a result, the switching device 24 is constructed so as to be rotatable about the coupling member 17 and water-tight.

The operation portion 6 is provided with: a display portion 61 for displaying images picked up by the imaging mechanism 3 and the results of measurements such as shape measurement; and a grip portion 62 for the user of the endoscope apparatus 1 to retain the operation portion 6. The operation portion 6 of the endoscope apparatus 1 of the first embodiment according to the present invention is further provided with a pointing, device 63 for operating a pointer, an icon, or the like displayed on the display portion 61.

Next, the working of the endoscope apparatus 1 of the first embodiment according to the present invention will be described.

When the endoscope apparatus 1 is in use, the operator of the endoscope apparatus 1 uses one of his or her hands to grip the grip portion 62 provided in the operation portion 6 shown in FIG. 1, and uses the other of his or her hands to grip the insertion portion 2. Then, the operator guides the imaging mechanism 3 provided at the distal end 2a of the insertion portion 2 to an observation target.

To direct the image pick-up field of the imaging mechanism 3 to an intended position on the observation target, the operator inclines the bending lever 8 in an intended direction, as shown in FIG. 2. Then, the pull arm 15 coupled to the distal end 8a of the bending lever 8 swings about the swinging center P1. This pulls some of the four pull members 5 toward the proximal end. As a result, the bending portion 4 fixed to the distal ends of the pull members 5 is bent. If the operator keeps the position of the bending lever 8 with the bending lever 8 being inclined, the bending portion 4 is retained in a bent state.

If the bending portion 4 is to be retained in a bent state for a long time or if a need arises to ungrip the bending lever 8 in a state with the bending portion 4 being bent, the operator rotates the switching grip 25, which is arranged between the insertion portion 2 and the operation portion 6, in a first rotational direction (the direction denoted with reference symbol X1 in FIG. 7).

Then, as shown in FIG. 7, the rotational movement (the movement denoted with reference numerals X1, X2 in FIG. 7) of the switching grip 25 is converted by the guide wall 27 of the cam member 26 to a linear movement (a movement denoted with reference numerals Y1, Y2 in FIG. 7) of the protrusion portion 23 formed in the relay member 20. As a result, the protrusion portion 23 linearly moves toward the swinging center P1 along the elongated holes 17b formed in the coupling member 17. Namely, the press portion 19 linearly moves toward the swinging center P1 along the elongated holes 17b formed in the coupling member 17.

Slightly before the protrusion portion 23 reaches the recess portion 27d (see FIG. 9) provided at the end on the proximal end side of the guide wall 27, the curved surface 22a of the stopper member 22 is brought into contact with the contact surface 18a. When the cam member 26 is rotated further in the first direction, the stopper member 22 is pressed against the contact surface 18a. Furthermore, when the protrusion portion 23 goes into the recess portion 27d, the stopper member 22 slightly returns toward the distal end while the stopper member 22 is kept in a state of being pressed against the contact surface 18a. As a result, the protrusion portion 23 is fitted into the recess portion 27d and retained there.

In a state with the stopper member 22 being pressed against the contact surface 18a, the friction member 18 as well as the pull arm 15 fixed to the friction member 18 is fixed with respect to the operation portion 6 via the press portion 19, the cam member 26, and the coupling member 17. As a result, the pull members 5 that are pulled by the pull arm 15 are fixed. Hence, the bending portion 4 is retained in a bent state without a retaining operation on the bending lever 8 by the operator.

When there is no need to retain the bent state of the bending portion 4 any longer, the switching grip 25 is rotated in the direction opposite to the first rotational direction (in the direction denoted with reference symbol X2 in FIG. 7) by the operator. This removes the protrusion portion 23 from the recess portion 27d (see FIG. 9). Furthermore, the protrusion portion 23 is guided by the guide wall 27 toward the distal end. As a result, the stopper member 22 of the press portion 19 is spaced away from the contact surface 18a.

As described above, according to the endoscope apparatus 1 of the first embodiment of the present invention, it is possible to press the press portion 19 against the contact surface 18a and to cause the press portion 19 to be spaced away from the contact surface 18a by the rotational operation of the switching grip 25. Therefore, it is possible to retain the bending portion 4 in a bent state, and also to make the operation portion 6 small.

Furthermore, the pull members 5 are arranged in the cutout 21 that are formed in the external surface of the relay member 20. This secures space for the pull members 5 to advance or retract. Therefore, it is possible to reduce the slide resistance of the pull members 5 to the relay member 20. Furthermore, in the first embodiment of the present invention, there are formed four cutouts 21, which are spaced from each other, in the external surface of the relay member 20. In addition, the four pull members 5 are contained in the cutouts 21 respectively. Therefore, in the range where the relay member 20 is arranged, the pull members 5 will not be entangled.

Furthermore, in the endoscope apparatus 1 of the first embodiment of the present invention, the switching device 24 is arranged at a position where the bending lever 8 is favorably operated by one hand and the switching device 24 is operated by the other hand. Therefore, compared with the case where the switching device 24 is operated by the hand that is operating the bending lever 8, the position of the bending lever 8 is steadier, leading to more favorable operability.

Furthermore, the switching device 24 is arranged at the proximal end 2b of the insertion portion 2. Therefore, the insertion portion 2 and the switching device 24, which are projections from the external surface of the operation portion 6, are placed together at one site. In addition, the switching device 24 is arranged at the proximal end 2b of the insertion portion 2. Therefore, in the posture of guiding the insertion portion 2 to an observation target by using the hand other than the one gripping the operation portion 6, moving the hand along the insertion portion 2 toward the proximal end 2b of the insertion portion 2 allows the hand to touch the switching grip 25 of the switching device 24. Consequently, it is possible to operate the switching grip 25 with ease without visually checking the position of the switching grip 25. As a result, there is no need to look away from the display screen of the display portion 61, and hence, it is possible to keep the possibility of loosing sight of observation targets low.

(Modified Example of First Embodiment)

Next is a description of a modified example of the endoscope apparatus 1 described in the aforementioned first embodiment. In the present modified example, the components common to those of the endoscope apparatus 1 described in the first embodiment are designated with the same reference symbols and are not repetitiously explained.

Figure 10:
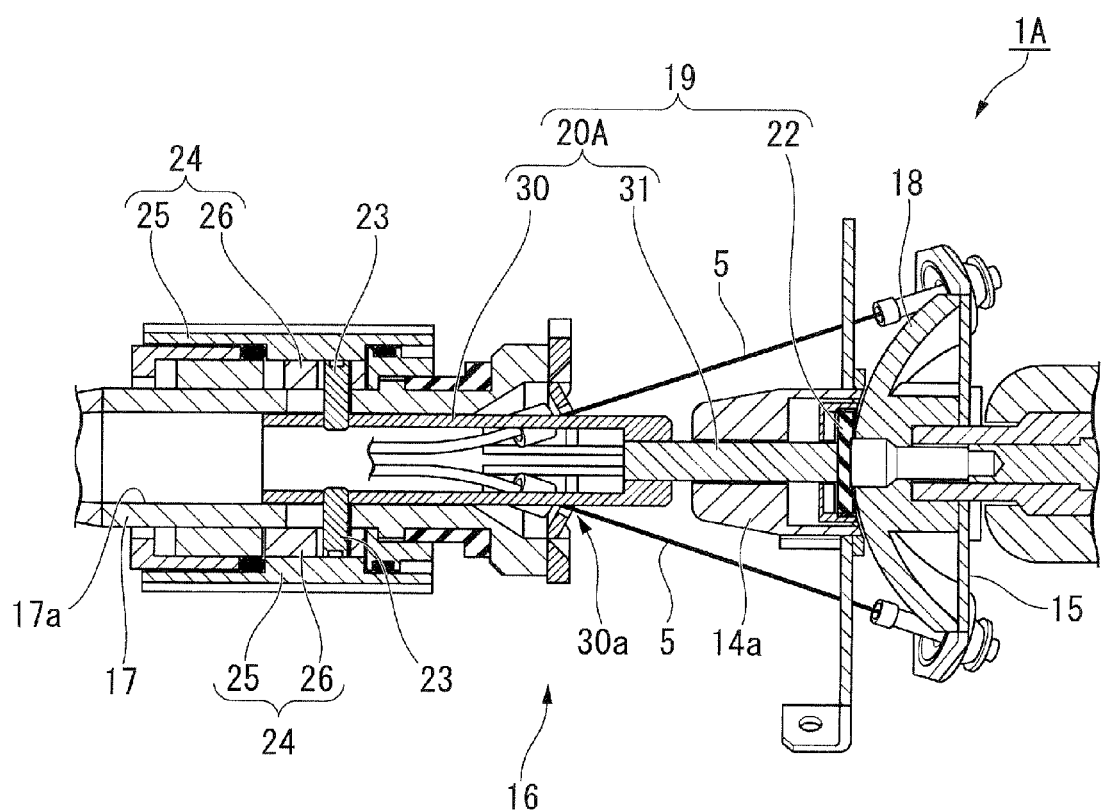
FIG. 10 is a cross-sectional view showing a configuration of a modified example of the first embodiment.

FIG. 10 is a cross-sectional view showing a configuration of the present modified example.

As shown in FIG. 10, an endoscope apparatus 1A is different in configuration from the endoscope apparatus 1 of the first embodiment in that a relay member 20A is used instead of the relay member 20.

The relay member 20A includes: a cylindrical portion 30 through which pull members 5 extend; and a stick-like portion 31 that is fixed to a proximal end of the cylindrical portion 30 and extends coaxially with the cylindrical portion 30. In the proximal end of the stick-like portion 31, there is fixed the stopper member 22 similar to that of the first embodiment. In the present modified example, an outer diameter of the stick-like portion 31 is smaller than that of the cylindrical portion 30.

The cylindrical portion 30 has a through-hole 30a that extends in parallel with a central axis line of the relay member 20A.

The through-hole 30a is open to a distal end face of the cylindrical portion 30 and to an outer circumferential surface of a proximal end of the cylindrical portion 30.

Out of an opening in the distal end face of the cylindrical portion 30 and also out of openings in the outer circumferential surface of the proximal end of the cylindrical portion 30, pull members 5 extend. The openings formed in the outer circumferential surface of the proximal end of the cylindrical portion 30 are an elongated holes that are longer in the direction of a central axis line of the cylindrical portion 30. Hence, even if the cylindrical portion 30 is advanced or retracted in a state with a bending lever 8 being inclined, edges of the openings are not pressed against the pull members 5.

In the present modified example, the number of the openings on the proximal end side of the cylindrical portion 30 is four. They are spaced 90 degrees apart about the central axis line of the cylindrical portion 30. The pull members 5 that extend out of the openings formed in the outer circumferential surface at the proximal end of the cylindrical portion 30 are directed to end portions 15a, 15b, 15c, and 15d of a pull arm 15.

The pull members 5 extending through the cylindrical portion 30 are arranged in parallel with the central axis line of the cylindrical portion 30.

In the present modified example, the cylindrical portion 30 has a cylindrical shape. A hole 17a formed in the coupling member 17 has a circular shape with a clearance that allows the cylindrical portion 30 to advance or retract. Therefore, the cylindrical portion 30 advance or retract along the hole 17a formed in the coupling member 17.

Even with this configuration, the present modified example has advantageous effects similar to those of the endoscope apparatus 1 of the first embodiment.

In addition, in the present modified example, the hole 17a formed in the coupling member 17 has a shape to fit an external surface of the cylindrical portion 30. Therefore, the external surface of the cylindrical portion 30 is unlikely to get stuck with an inner surface of the hole 17a, allowing the relay member 20A to smoothly advance or retract.

Furthermore, in the first modified example, the openings on the proximal end side of the cylindrical portion 30 are formed in a shape of an elongated hole that is longer in the direction of the central axis line. Therefore, even if the cylindrical portion 30 is advanced or retracted, the cylindrical portion 30 does not interfere with the pull members 5. Hence, the bent state of the bending portion 4 produced by the pull members 5 does not undergo an unintentional change.

(Second Embodiment)

Next is a description of an endoscope apparatus 1 of a second embodiment of the present invention. In the second embodiment of the present invention, the constituent elements common to those of the endoscope apparatus 1 and the endoscope apparatus 1A that have been described in the first embodiment and its modified example are designated with the same reference symbols, and are not repetitiously explained.

Figure 11:
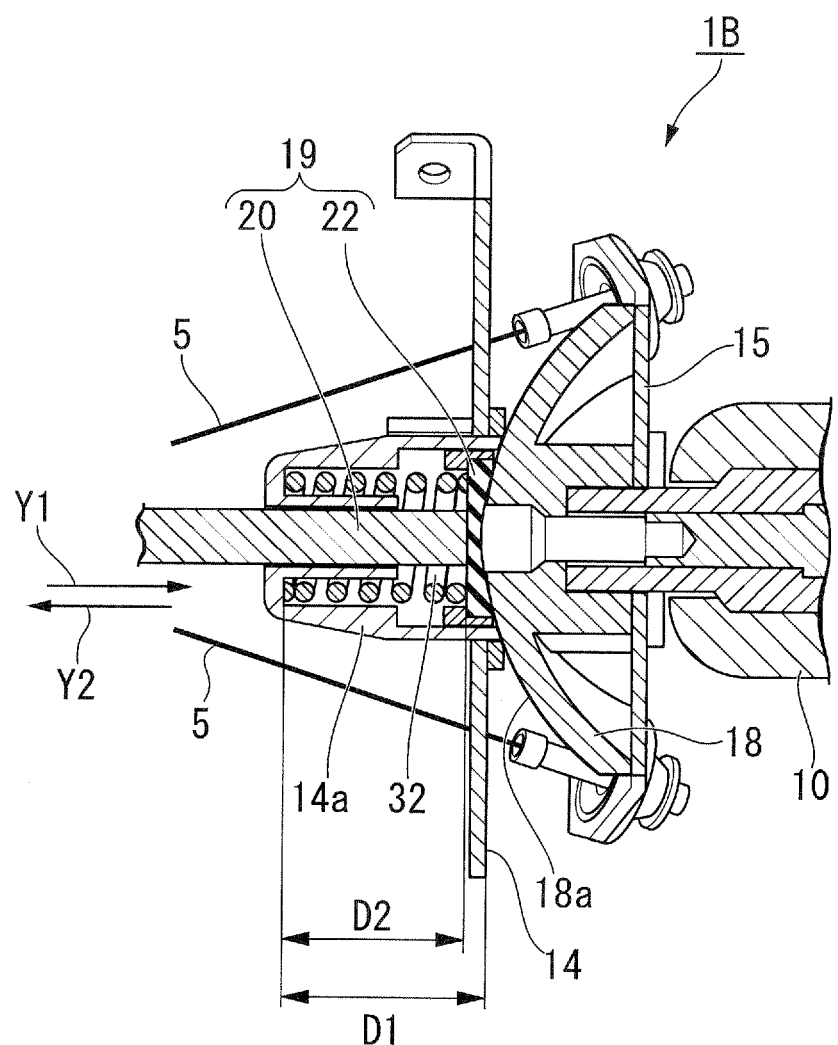
FIG. 11 is a diagram showing a configuration of an endoscope apparatus of a second embodiment according to the present invention, that is, a cross-sectional view showing a part of an internal configuration of an operation portion.

FIG. 11 is a diagram showing a configuration of an endoscope apparatus of the second embodiment of the present invention, namely, a cross-sectional view showing a part of an internal configuration of an operation portion.

As shown in FIG. 11, an endoscope apparatus 1B of the second embodiment of the present invention further includes a biasing member 32 that biases a press portion 19 toward the contact surface 18a. Furthermore, a switching device 24 is configured as follows. When a switching grip 25 is rotated in a second rotational direction (in a direction denoted with reference numeral X2 in FIG. 7), the switching device 24 pulls the press portion 19 away from the contact surface 18a while resisting the biasing force by the biasing member 32.

To be more precise, the biasing member 32 is a spring whose one end is fixed to a housing 14a and whose other end is fixed to a stopper member 22. As the biasing member 32 in the second embodiment of the present invention, a compression coil spring is adopted that, while advancing-and-retracting driving force is not applied to the relay member 20, brings the stopper member 22 into contact with the contact surface 18a and is set in a compressed state by the resistance from the contact surface 18a. Furthermore, the biasing member 32 is a coil spring with a natural length longer than a distance D1 from the housing 14a to the contact surface 18a. In a state with the stopper member 22 abutting the contact surface 18a, the biasing member 32 is compressed so as to have a length of D2 which is shorter than the distance D1.

Namely, in the second embodiment of the present invention, the biasing member 32 presses the stopper member 22 against the contact surface 18a in a state with no external force being applied.

The other end of the biasing member 32 is fixed to a distal end surface of the stopper member 22 around a central portion to which the relay member 20 is fixed. As a result the biasing member 32 biases a circumferential edge of the stopper member 22 at the distal end surface to the contact surface 18a side.

Next, a working of the endoscope apparatus 1B of the second embodiment will be described.

In the second embodiment, the relay member 20 fixed to the stopper member 22 is biased to the direction of the proximal end (to the friction member 18 side) by the biasing member 32. In the second embodiment, a protrusion portion 23 is in engagement with a guide wall 27 of a cam member 26, similarly to the first embodiment. Therefore, when the switching grip 25 is rotated in the second rotational direction (the direction denoted with reference symbol X2 in FIG. 7), the protrusion portion 23 moves in a direction of the distal end of the switching device 24 while resisting the biasing force of the biasing member 32 (see FIG. 7 and FIG. 11). Accordingly, the relay member 20 and the stopper member 22 fixed to the relay member 20 are pulled toward the distal end, causing the stopper member 22 to be spaced away from the contact surface 18*a* of the friction member 18.

Contrary to this, when the switching grip 25 is rotated in the first rotational direction (the direction denoted with reference symbol X1 in FIG. 7), the pull of the relay member 20 and the stopper member 22 is released, and the stopper is pressed against the contact surface 18*a* of the friction member 18 through the restorative force of the biasing member 32.

In the second embodiment of the present invention, the stopper member biased to the contact surface 18*a* by the biasing member 32. Therefore, even if the stopper member 22 is worn out, the force pressing the stopper member 22 against the contact surface 18*a* is maintained.

Furthermore, even if the distance between the stopper member 22 and the contact surface 18*a* is not uniform due to an error produced when the endoscope apparatus 1B is processed on or assembled, the force pressing the stopper member 22 against the contact surface 18*a* is maintained in the range where the biasing member 32 is extendable.

Furthermore, because the biasing member 32 biases the circumferential edge of the stopper member 22 at the distal end face to the contact surface 18*a*, the stopper member 22 is pressed against the contact surface 18*a* not only b) the force of the relay member 20 pressing the center of the distal end face of the stopper member 22 but also by the force of the relay member 20 pressing the circumferential edge of the distal end face of the stopper member 22. Therefore, it is possible to increase the frictional force between the stopper member 22 and the contact surface 18*a*. Moreover, it is also possible to prevent the proximal end face of the stopper member 22 from wearing out only at its central portion.

(Modified Example of Second Embodiment)

Next is a description of a modified example of the endoscope apparatus 1B of the second embodiment of the present invention.

In the present modified example, as a mechanism for pulling the relay member 20 toward the distal end, a mechanism of using a wire to pull the relay member 20 toward the distal end is provided instead of the mechanism made of the cam member 26 and the protrusion portion 23. The configuration other than this is similar to that of the endoscope apparatus 1B described in the aforementioned second embodiment.

Figure 12:
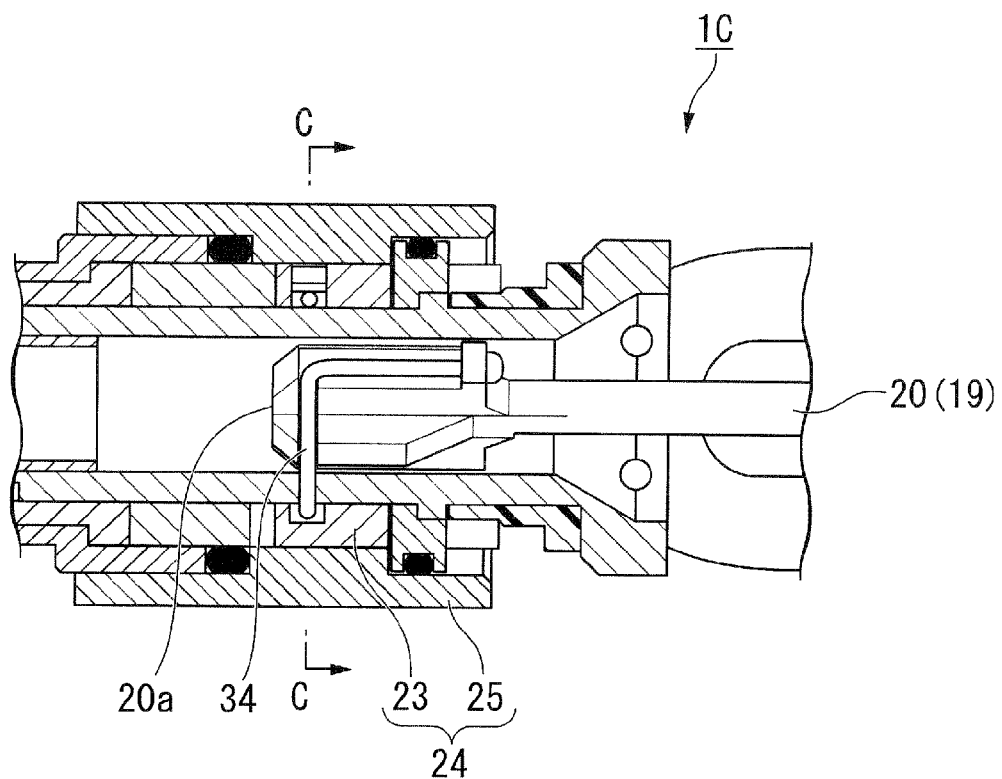
FIG. 12 is a partial cross-sectional view showing a configuration of a modified example of the second embodiment.
Figure 13:
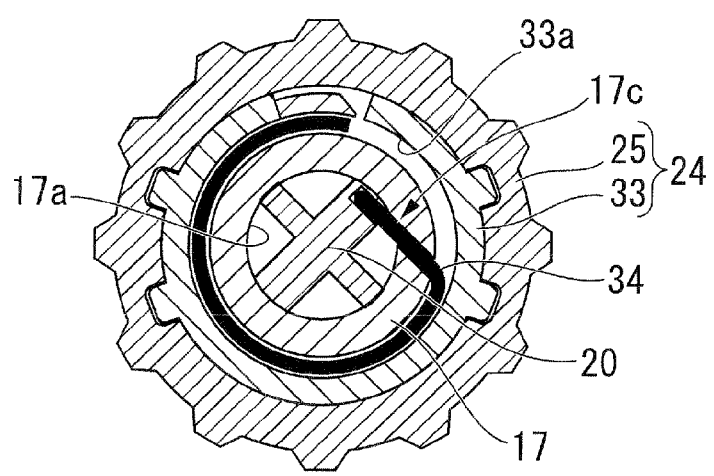
FIG. 13 is a cross-sectional view of FIG. 12, taken along the line C-C.

FIG. 12 is a partial cross-sectional view showing a configuration of the present modified example. FIG. 13 is a cross-sectional view of FIG. 12, taken along the line C-C.

As shown in FIG. 12 and FIG. 13, in an endoscope apparatus 1C of the present modified example, a pull ring 33 formed with a guide groove 33*a* extending in a circumferential direction is fixed to a switching grip 25, instead of the cam member 26. In the guide groove 33*a* of the pull ring 33, a wire 34 is arranged with flexibility. One end of the wire 34 is fixed to the pull ring 33, and the other end of the wire 34 is led into a hole of a coupling member 17 to be fixed to the relay member 20. In the present modified example, the position at which the wire 34 is fixed to the relay member 20 is located closer to the proximal end than a lead-in hole 17*c* that is formed in the coupling member 17 for leading the wire 34 therein.

In the present modified example, when the switching grip 25 is rotated in the second rotational direction, the one end of the wire 34 is pulled in a circumferential direction of the pull ring 33. As a result, the relay member 20 fixed to the other end of the wire 34 moves linearly along the hole 17*a* so as to be closer to the position of the pull ring 33. In the present modified example, because the position at which the wire 34 is fixed to the relay member 20 is located closer to the proximal end than the lead-in hole 17*c* formed in the coupling member 17 for leading the wire 34 therein, the relay member 20 is pulled toward the distal end of the coupling member 17.

Then, similarly to the case described in the second embodiment, the stopper member 22 is pulled toward the distal end while resisting the biasing force of the biasing member 32. This causes the stopper member 22 to be spaced away from the contact surface 18*a* of the friction member 18.

Contrary to this, when the switching grip 25 is rotated in the first rotational direction, the stopper member 22 and the relay member 20 move toward the proximal end by the restorative force of the biasing member 32. At this time, the wire 34 is pulled by the relay member 20. Therefore, the wire 34 is led into the hole 17*a* of the coupling member 17 through the lead-in hole 17*c* without being deflected in the guide groove 33*a*.

Even with the configuration of the present invention, the present modified example has advantageous effects similar to those described in the second embodiment.

While the embodiments of the present invention have been described in detail with reference to the drawings, specific configurations are not limited to the embodiments. Design modifications can be made without departing from the spirit or scope of the invention.

For example, in the aforementioned embodiments, the illustration has been for the case where the protrusion portion provided in the relay member is a pin with a length longer than the outer diameter of the distal end of the relay member, by way of example. However, the configuration of the protrusion portion is not limited to this. For example, the protrusion portion may be a part of the relay member and formed integrally therewith. Furthermore, the protrusion portion may protrude outwardly only at a single location on the external surface of the relay member.

It is preferable that the pitch of the spiral in the guide wall formed in the cam member be set in consideration of the rotational force required to rotate the switching grip and also in consideration of the pressing force for pressing the stopper member against the contact surface. With a small pitch of the spiral in the guide wall, the switching grip can be rotated with a weak force when it is rotated to press the stopper member against the contact surface.

Furthermore, the guide wall formed in the cam member may extend one turn or longer in the circumferential direction of the cam member.

The components shown in the aforementioned embodiments and modifications may be appropriately combined.

It should be understood that these are exemplary of the invention and are not to be considered as limiting. Additions, omissions, substitutions, and other modifications can be made without departing from the spirit or scope of the present invention. The present invention is not to be considered as limited by the foregoing description and is only limited by the scope of the appended claims.

What is claimed is:

1. An endoscope apparatus comprising:
   an insertion portion;
   a bending portion provided at a distal end of the insertion portion;
   an operation portion provided at a proximal end of the insertion portion and configured to perform a bending operation for bending the bending portion;
   a pull member configured to connect the bending portion to the operation portion and configured to be pulled by the bending operation by the operation portion, to thereby bend the bending portion; and a bent state retention mechanism which retains the bending portion in a desired bent state, the bent state retention mechanism being arranged between the operation portion and the insertion portion;

wherein the operation portion comprises:
- a joystick which is supported so as to be freely inclinable about a predetermined swinging center and to which the bending operation for bending the bending portion is input; and
- a friction member that is fixed to the joystick and on which a partially spherical contact surface is formed, a center of the contact surface being the swinging center; and wherein the bent state retention mechanism comprises:
- a relay member arranged on and extending in a direction of an axis line including the swinging center, the relay member being movable along the axis line and comprising (i) a stopper portion which is provided at a proximal end of the relay member and which stops motion of the joystick when the stopper portion comes into contact with the friction member, and (ii) a protrusion portion which is provided at a distal end of the relay member and which extends in a direction perpendicular to the axis line;
- a grip member comprising a cylindrical member arranged along the axis line so as to surround the relay member and the pull member, an outer circumferential surface of the grip member being adapted to be gripped by a user, and the grip member being rotatable about the axis line as a rotation center; and
- a cam member formed with a guide wall which forms a part of a spiral about the axis line and which engages with the protrusion portion, the cam member being rotatable with respect to the relay member about the axis line as a rotation center in accordance with rotation of the grip member;

wherein:
- when the grip member is rotated in a first rotational direction about the axis line, the relay member is moved toward the swinging center along the axis line and the stopper portion comes into contact with the friction member; and
- when the grip member is rotated in a second rotational direction about the axis line which is opposite to the first rotational direction, the relay member is moved in a direction away from the swinging center along the axis line and the stopper portion is spaced away from the friction member.

2. The endoscope apparatus according to claim 1, wherein the protrusion portion protrudes from an external surface of the relay member outwardly in a radial direction of the relay member.

3. The endoscope apparatus according to claim 2, wherein the external surface of the relay member has a cutout that extends in parallel with the axis line, and wherein a part of the pull member is contained in an internal portion of the cutout and is arranged in parallel with the axis line.

4. The endoscope apparatus according to claim 2, wherein the relay member further comprises a through-hole that extends in parallel with the axis line and opens at both ends, and wherein a part of the pull member is inserted into the through-hole and is arranged in parallel with the axis line.

5. The endoscope apparatus according to claim 1, further comprising a biasing member configured to bias the stopper portion toward the contact surface, wherein when the grip member is rotated in the second rotational direction, the stopper portion is caused to be pulled away from the contact surface while resisting a biasing force of the biasing member.

6. The endoscope apparatus according to claim 1, wherein the relay member is formed such that when the grip member is rotated in the first rotational direction, the stopper portion comes into contact with the friction member before the protrusion portion comes into contact with a proximal end of the guide wall of the cam member.

7. The endoscope apparatus according to claim 1, wherein a length of the guide wall of the cam member in a circumferential direction of the cam member is less than one turn of the grip member.

8. The endoscope apparatus according to claim 1, further comprising a coupling member, the coupling member comprising a cylindrical member having a hole formed therethrough along the axis line for communicating an internal portion of the insertion portion with an internal portion of the operation portion, wherein the pull member and the relay member are inserted inside the hole along a direction parallel to the axis line, and wherein the coupling member supports the relay member such that the relay member is movable along the axis line.

9. The endoscope apparatus according to claim 1, further comprising a plurality of O-rings arranged between an inner circumferential surface of the grip member and an outer circumferential surface of the coupling member and provided at opposite ends of the cam member in a direction of the axis line.

10. The endoscope apparatus according to claim 1, wherein a hollow portion is formed in the relay member along the direction of the axis line and a lead line is inserted into the hollow portion.

11. The endoscope apparatus according to claim 1, further comprising a coil spring which biases the stopper portion towards the friction member, wherein the coil spring is arranged so as to be wound around the relay member extending along the direction of the axis line.

* * * * *